(12) United States Patent
Estrada, Jr.

(10) Patent No.: US 7,367,977 B2
(45) Date of Patent: May 6, 2008

(54) APPARATUS FOR DYNAMIC EXTERNAL FIXATION OF DISTAL RADIUS AND WRIST FRACTURES

(76) Inventor: Hector Mark Estrada, Jr., 13121 Troops Trail, Austin, TX (US) 78727

( * ) Notice: Subject to any disclaimer, the term of this patent is extended or adjusted under 35 U.S.C. 154(b) by 414 days.

(21) Appl. No.: 10/377,094

(22) Filed: Feb. 28, 2003

(65) Prior Publication Data
US 2003/0225407 A1 Dec. 4, 2003

Related U.S. Application Data

(60) Provisional application No. 60/360,443, filed on Feb. 28, 2002.

(51) Int. Cl.
*A61F 2/42* (2006.01)
(52) U.S. Cl. ............... 606/54; 606/53; 606/55; 606/56; 606/57; 606/58; 606/59
(58) Field of Classification Search ............... 606/54, 606/55, 57, 59, 105
See application file for complete search history.

(56) References Cited

U.S. PATENT DOCUMENTS

| | | | |
|---|---|---|---|
| 4,893,618 A * | 1/1990 | Herzberg ............ 606/54 |
| 5,437,667 A | 8/1995 | Papierski et al. |
| 5,443,464 A | 8/1995 | Russell et al. |
| 5,630,815 A * | 5/1997 | Pohl et al. ............ 606/59 |
| 5,676,664 A | 10/1997 | Allard et al. |
| 5,725,526 A | 3/1998 | Allard et al. |
| 5,728,095 A * | 3/1998 | Taylor et al. ............ 606/54 |
| 5,976,125 A | 11/1999 | Graham |
| 5,976,134 A * | 11/1999 | Huebner ............ 606/59 |
| 6,171,309 B1 | 1/2001 | Huebner |
| 6,491,694 B1 * | 12/2002 | Orsak ............ 606/57 |
| 6,613,049 B2 | 9/2003 | Winquist et al. |

* cited by examiner

*Primary Examiner*—Corrine McDermott
*Assistant Examiner*—David A. Izquierdo
(74) *Attorney, Agent, or Firm*—Gregory K. Goshorn; Greg Goshorn, P.C.

(57) ABSTRACT

The fixator is an apparatus for repairing fractures of the distal radius and wrist. Distal, pivot, distraction, and radial members provide an anatomically contoured, radiolucent apparatus that permits the wrist to move through a substantially normal range of motion. A means for distraction of the bones by the fixator is also provided. The fixator may be affixed to the lower arm and hand by spaced-apart elongate distal mounting pins with lower ends adapted or mounting in the metacarpal bone and by spaced-apart elongate radial mounting pins with lower ends adapted for mounting in the radius.

18 Claims, 12 Drawing Sheets

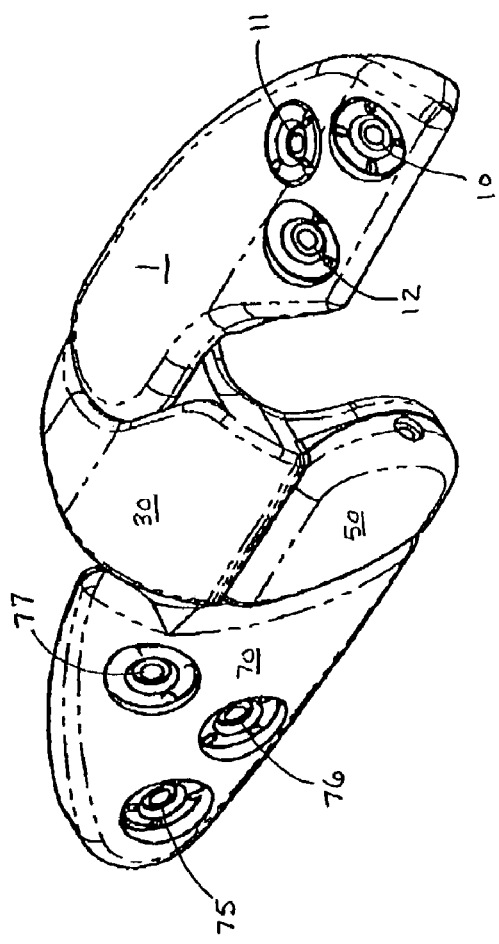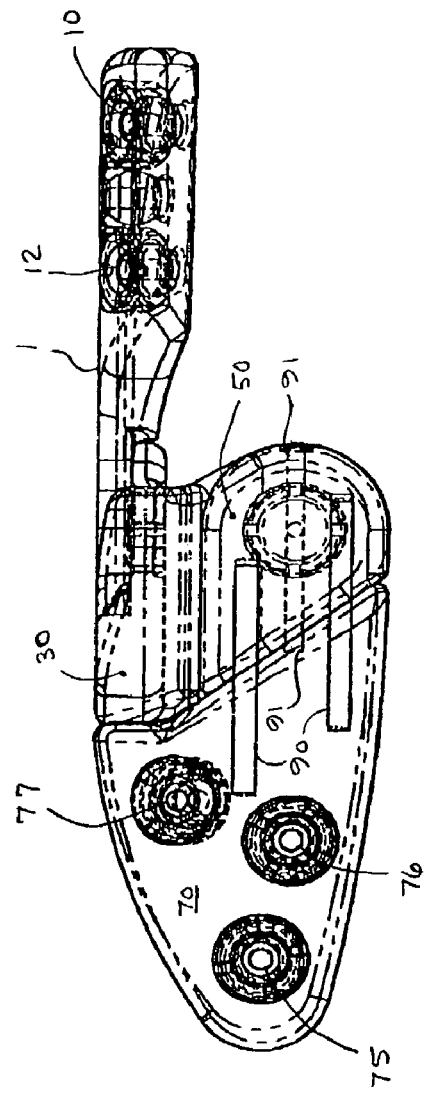
FIG 1B
FIG 1A

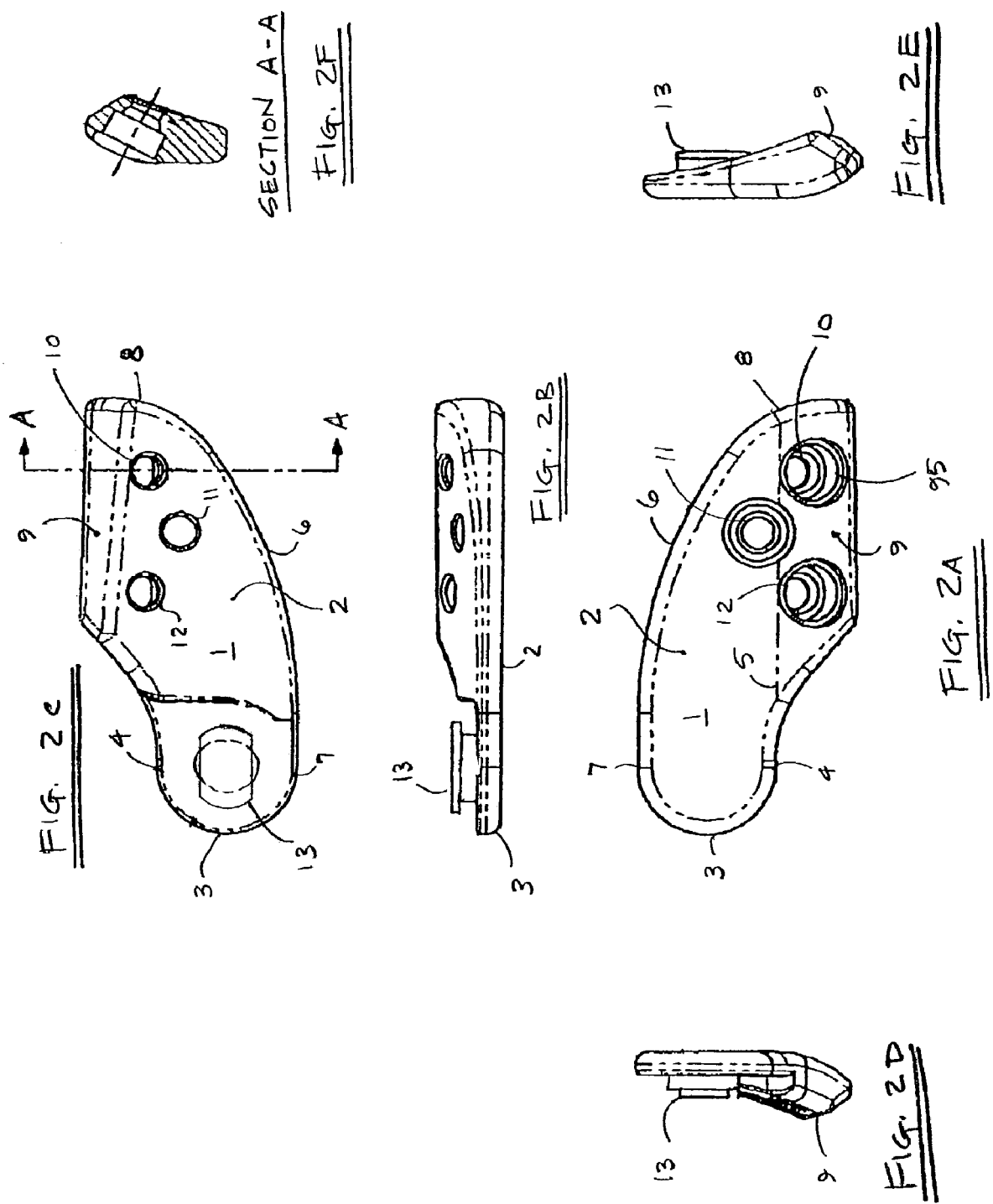

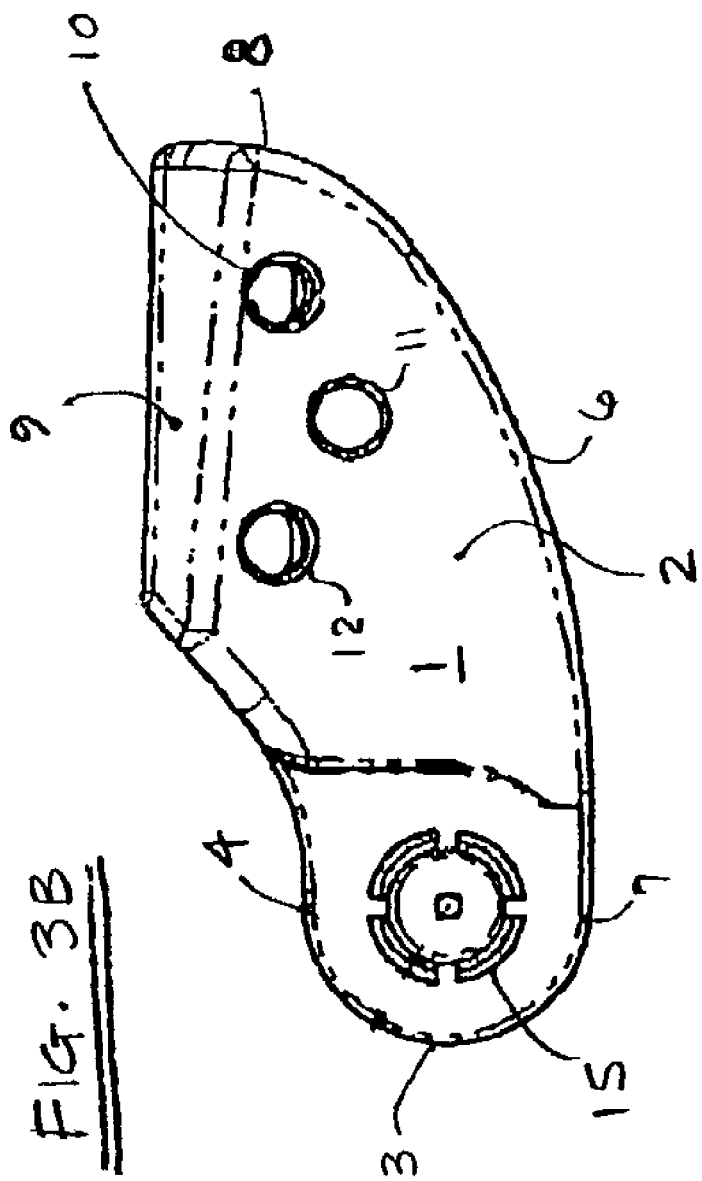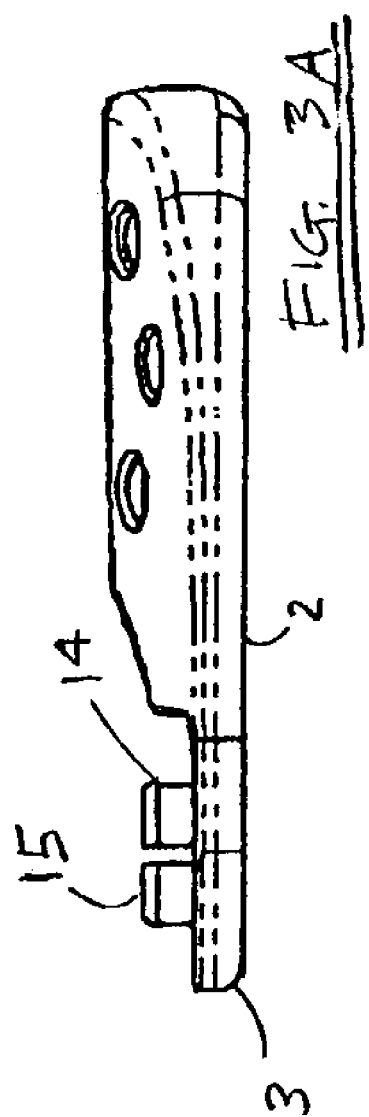

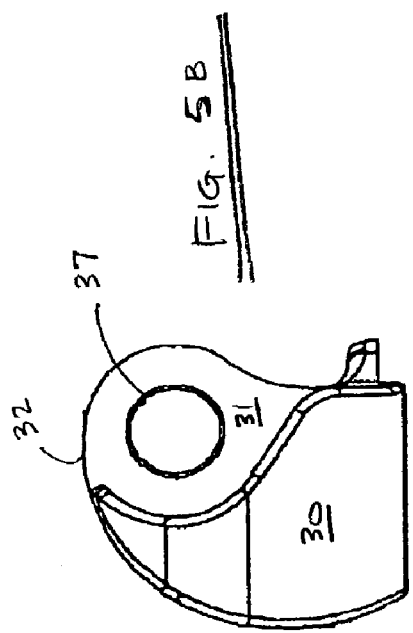
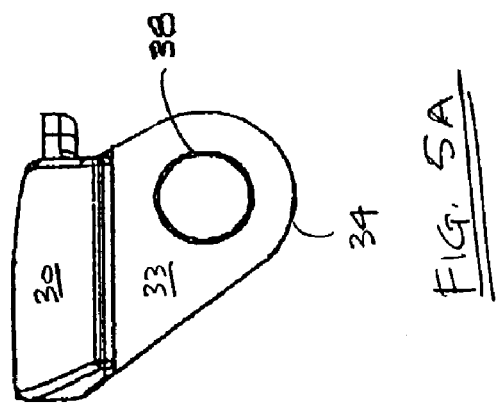

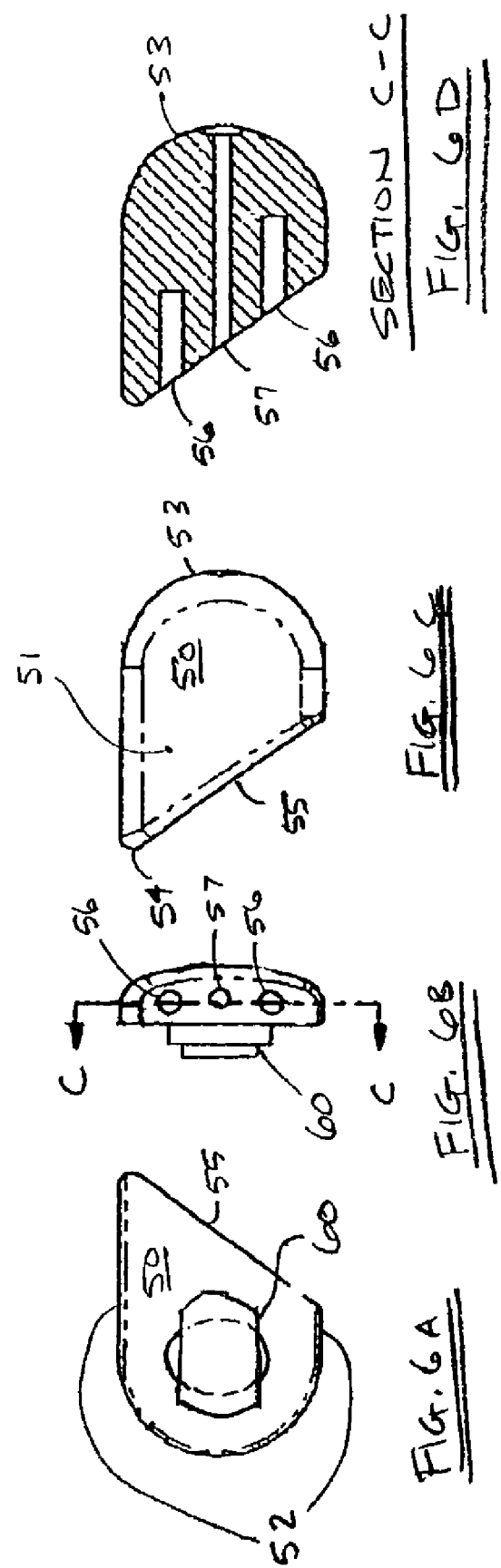

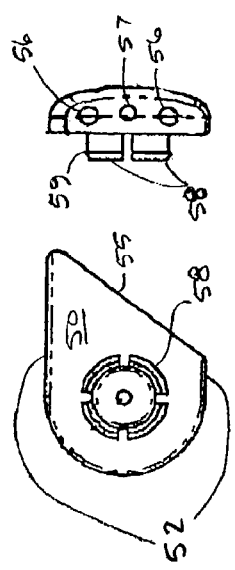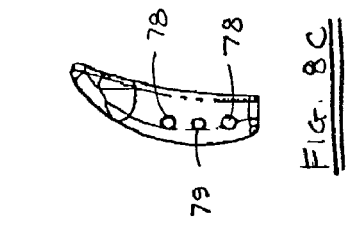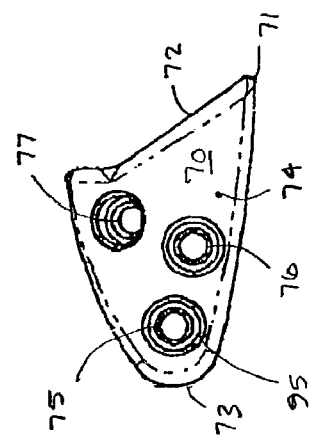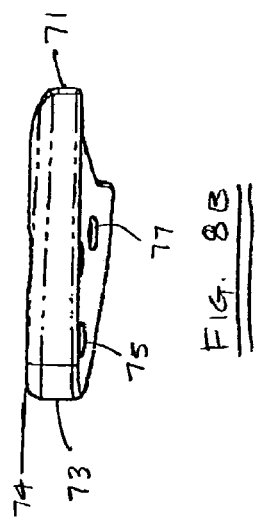

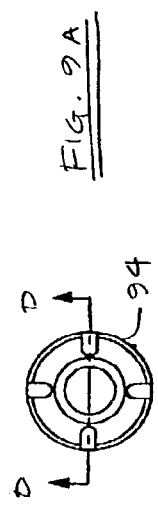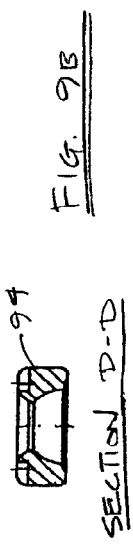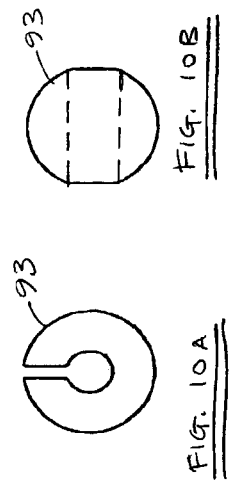

APPARATUS FOR DYNAMIC EXTERNAL FIXATION OF DISTAL RADIUS AND WRIST FRACTURES

RELATED APPLICATIONS

This application claims the benefit of U.S. Provisional Application No. 60/360,443 filed 28 Feb. 2002.

FIELD OF THE INVENTION

The present invention relates generally to a dynamic bone fixator for repairing fractures of the distal radius and wrist. More particularly, the present invention is adapted to reduce and stabilize the relative positions of the fractured bone at the fracture site to promote proper healing and recovery.

BACKGROUND OF THE INVENTION

The first external fixator was developed for reducing and maintaining patellar fractures. Since that time, various fixators have been invented for splinting various bone fractures. Most of these fixators have common features. In particular, they rely on transcutaneous pins or screws secured in the bone on either side of the fracture site. An external apparatus is attached to the pins to allow their relative positions to be adjusted, thus enabling a surgeon to reestablish alignment of the bone pieces at a fracture site. Once the bone is properly set, the articulations in the fixator may be locked into place to maintain the chosen alignment.

Principal variations among the many fixator designs include the number of degrees of freedom permitted the wrist and the relative independence of each articulation, both mechanical and geometric. The first external fixator, for instance, was adjustable only in length and squeezed the fracture together by gripping opposed ends of the patella. Fixators designed to repair central fractures of the long bones typically have relatively few articulations or degrees of freedom. In contrast, fixators adapted to treat fractures of bones in joint regions must permit articulation through many more degrees of freedom. Where there is insufficient room to place pins in the bone fragment between the fracture and the joint, bone alignment must be established using pins placed in a bone on the side of the joint opposite the fracture. Such treatment of fractures near joints such as the wrist, which can rotate, flex and abduct, requires that a fixator permit some movement through the range of motion of the joint in a manner allowing a surgeon to establish proper fracture alignment by using forces transmitted through the joint.

Modem fixators permit articulation by various methods. Probably the most common articulation is provided by a ball joint. A ball joint provides one rotational and two pivotal degrees of freedom. A single setscrew or other locking mechanism can fix all three degrees of freedom simultaneously. The disadvantage of this method of articulation is that it is not possible to loosen the joint to permit motion in only one of the possible degrees of freedom. Thus, a surgeon cannot loosen the ball joint slightly to pivot it a small amount in one direction without the possibility of introducing changes affecting the other pivot and rotation settings.

In order to overcome this limitation, some fixators eliminate ball joints and rely instead on a combination of independent articulations to provide the necessary freedom of movement. The benefit of such a system is that each degree of freedom is mechanically independent of every other degree of freedom. A surgeon may thus adjust the position of a single articulation in the fixator without affecting the settings of other articulations.

Most fixators also include some type of extensible/contractible articulation to permit the longitudinal spacing between the pins on opposite sides of the fracture to be controlled. This type of translational freedom can be used to accommodate individuals of varying size, as well as to distract the fracture, if necessary.

The wrist joint permits the hand to move in three degrees of freedom relative to the forearm. First, the hand can move in supination and pronation, i.e., the rotation about the longitudinal axis of the forearm. Second, the hand can move in adduction and abduction, i.e., lateral flexion, or pivoting about an axis perpendicular to the plane of the palm. The last type of mobility of the hand is dorsal-palmar flexion, which is the pivotal motion about an axis in the plane of the palm and perpendicular to the longitudinal axis of the forearm.

Dynamic fixators allow for some movement while affixed to a joint region, such as a lower arm, wrist and hand, yet maintain sufficient alignment of the fracture while it heals. Such prescribed movement can reduce and assist in recovery from stiffness associated with immobilization of the fracture.

Fixators have typically been designed from a purely functional viewpoint. Fixator design and construction has generally been bulky and unsightly, and generally increase the effective dimensions of the wearer's hand, wrist and arm to an awkward degree. Further, these fixators have typically been far more robustly designed than is necessary. The size and weight of these fixators thus add an undesirably bulky and clumsy addition to the wearer's arm and hand.

One of the more common fractures requiring a fixator for proper treatment is a fracture of the distal radius, or Colles fracture. This type of fracture usually results from a fall upon an outstretched hand. The fracture line is usually quite close to the distal head of the radius and sometimes the head is comminuted. Because of the lack of space and the number of tendons and nerves in the area, it is difficult to mount pins in the radius on the distal side of the fracture. Therefore, such fractures are typically reduced using a pair of pins set in the index, or second metacarpal and a pair of pins set in the radius on the proximal side of the fracture. In order to avoid damage to tendons and nerves, the radial pins are usually set in the third quarter of the radius, i.e., the proximal half of the distal half of the radius. With the pins are set on opposite sides of the wrist joint, the fixator must be sufficiently articulate to reduce the fracture using forces transmitted through the wrist joint.

SUMMARY OF THE INVENTION

The present invention is an apparatus for dynamic external fixation of the distal radius and wrist for fracture repair. A pivot member provides two planes through which the wrist may move, namely, dorsal-palmar flexion and lateral flexion. A distal member pivotably connected to a pivot member provides a plurality of pin-mounting holes for fixation of the apparatus to pins set in the index metacarpal. A distraction member, pivotably connected at one end to the pivot member and translationally connected to a radial member at the other end, provides a means for distraction of the affected bones by means of a threadably advanceable screw to promote healing by proper alignment and spatial reduction of the fracture. The radial member further provides a plurality of pin-mounting holes for fixation of the apparatus to pins set in the radius. The invention is affixed to the human lower arm and hand by spaced-apart elongate distal mounting pins having one end adapted for mounting in the metacarpal bone and spaced-apart elongate radial mounting pins having one end adapted for mounting in the radius.

Visual indication of the degree of angular displacement of the pivoting members may be provided by graduations marked into the pivoting members. Visual indication of the translational separation between the distraction and radial members may be provided by a graduated tab situated along the line of translation.

Set screws are provided to limit or prevent, if necessary, the angular displacement of the pivoting members.

The present invention is further designed to address the psychological impact of the fixator on the patient to whom it is affixed. The awkward profile and bulk of a fixator may be distressing to the wearer, as well as to other people who may come into contact with the wearer, particularly during meals and in public. It is therefore desirable to mitigate the deleterious psychological impact of wearing a fixator, to whatever extent possible, yet allow for medical examination, e.g., visually or by x-ray, without disturbing the fixator.

It is therefore an object of the present invention to provide a dynamic external fixator for use on fractures of the distal radius or wrist.

It is another object of the present invention to provide a dynamic external fixator for use on fractures of the distal radius that is articulated to permit the wrist to move through a substantially normal range of motion.

It is an additional object of the present invention to provide a dynamic external fixator, for use on fractures of the distal radius, that provides a sufficient range of mobility to accommodate wrist flexibility and imprecise pin placement yet still have sufficient range of motion to reduce the fracture.

It is yet another object of the present invention to provide a dynamic external fixator for use on fractures of the distal radius with sufficient free articulations to facilitate easy mounting of the fixator pins set in the radius and metacarpal bones.

An additional object of the present invention is to provide a dynamic external fixator for use on fractures of the distal radius that allows a surgeon to achieve accurate and rapid reduction of the fracture.

A further object of the present invention is to provide a dynamic external fixator for use on fractures of the distal radius that allows a surgeon to achieve accurate and rapid distraction of the fracture.

Another object of the present invention is to provide a dynamic external fixator of relatively light weight having an anatomy-conforming, low profile for functional and cosmetic appeal.

It is an object of the present invention to provide an anatomy-conforming, low profile by utilizing members having a generally plate-like configuration.

Another object of the present invention is to provide a dynamic external fixator comprised, in whole or in part, of a radiolucent material, such as polycarbonate.

Another object of the present invention is to provide a dynamic external fixator comprised, in whole or in part, of a transparent material.

These and other objects and advantages will become apparent from a consideration of the accompanying drawings and ensuing description.

BRIEF DESCRIPTION OF THE DRAWINGS

FIGS. 1A-1E are various views of an assembled fixator of the present invention.

FIGS. 2A-2F are various views of the distal member, in a keyhole engagement embodiment.

FIGS. 3A-3B are various views of the distal member, in a snap-in engagement embodiment.

FIGS. 5A-5B are various views of the pivot member, in a snap-in engagement embodiment.

FIGS. 6A-6D are various views of the distraction member, in a keyhole engagement embodiment.

FIGS. 7A-7B are various views of the distraction member, in a snap-in engagement embodiment.

FIGS. 8A-8D are various views of the radial member.

FIGS. 9A-9B are various views of a ball cap.

FIGS. 10A-10B are various views of a pin ball.

FIG. 11 depicts a rail.

Even though the present invention is described with reference to the drawings and certain embodiments, it will be understood that such description is not intended to limit the invention to those embodiments. Rather, those skilled in the art will appreciate that the claims appended hereto are intended to broadly cover all alternatives, modifications, and equivalents reasonably understood to fall within their scope.

DETAILED DESCRIPTION OF THE INVENTION

Figure 12:
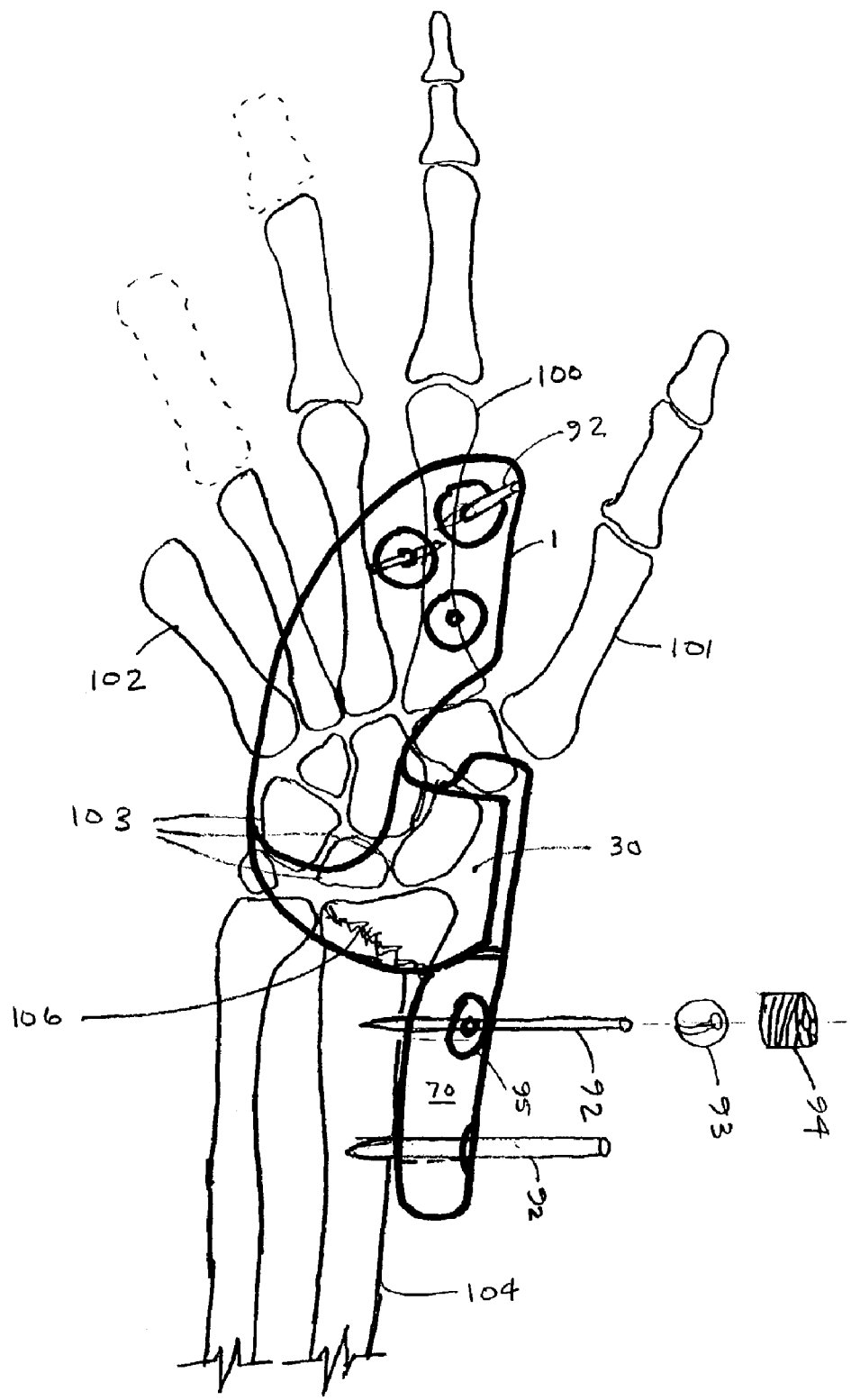
FIG. 12 depicts placement of a fixator of the present invention with respect to a human hand in dorsal (plan) view.
Figure 13:
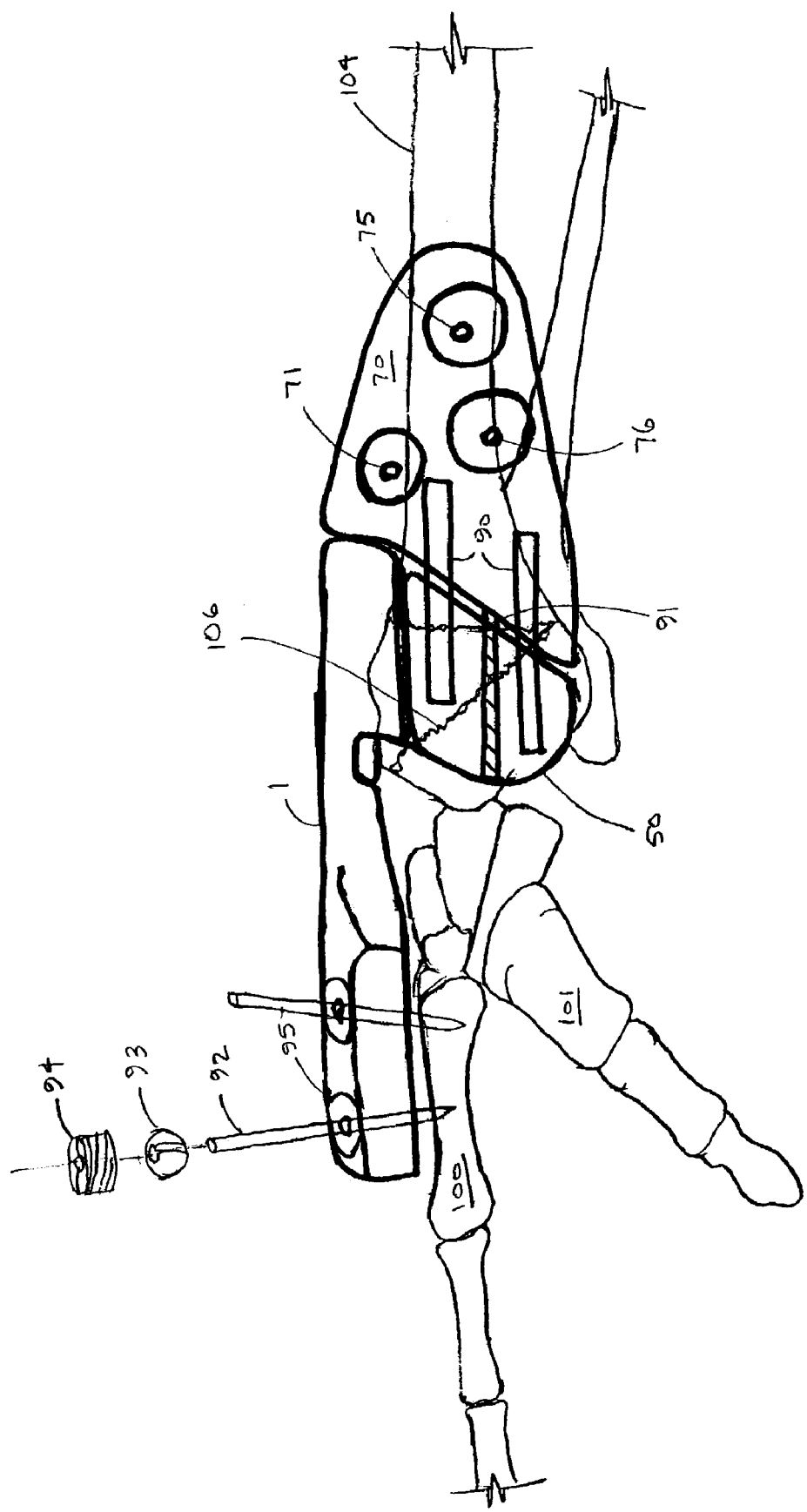
FIG. 13 depicts placement of a fixator of the present invention with respect to the human hand in an elevational view.

As may best be seen in FIGS. 1A-1F, the present invention is comprised of four primary members, a distal member 1, a pivot member 30, a distraction member 50, and a radial member 70, which generally embody an anatomy-conforming, plate-like configuration. These members, as more fully described below, are assembled such that the major plane 2 of the distal member 1 is generally perpendicular to the major plane 51 of the distraction member 50 and the major plane 74 of the radial member 70. Such assembly, when fixed by pins 92 to the human wrist about a fracture 106, as seen in FIGS. 12 and 13, preferably permits the wrist to move through a substantially normal range of motion, namely, in palmar-dorsal flexion (up-down), lateral (side-to-side) flexion, and supination-pronation (rotational) flexion. Each of the primary members are preferably comprised, in whole or in part, of radiolucent material. For ease of reference, each primary member is defined, in part, by its respective desired orientation to the human hand, wrist, and/or arm.

The present invention is best described with respect to the human hand, wrist and arm when the arm is placed on a flat surface, such as a typical hospital operating table, in a manner that permits the palm of the hand to face and contact the flat surface, such that the index (second) metacarpal 100 is coaxially aligned with the radius 104, as in FIG. 12. Again, for ease of reference, each primary member is described individually with respect to its orientation to the hand, wrist or arm, and then described with respect to the other primary members, i.e., assembled.

The distal member 1 is provided with multiple points for fixation of the dynamic external fixator to the index metacarpal 100, as may be seen in FIGS. 2A-2F, 12 and 13. The distal member 1 is generally planar, which major plane 2 is oriented generally parallel to the dorsal aspect of the hand, and which long axis is further generally aligned with the index metacarpal 100. The first, or arm-facing, end 3 of the distal member 1 is defined by a semicircle of given radius. A first end 4 of the semicircle defines the first end of a line tangent 5 to the semicircle at that point, such tangent line 5 being parallel to the long axis of the distal member 1. A tapering curve 6 of varying radii extends from the second end 7 of the semicircle to intersect the tangent line 5 at a near perpendicular angle so as to define the distal member 1 edge facing the fifth metacarpal 102 (little finger). The intersection of the tapering curve 6 and the tangent line 5 generally defines the second end 7 of the distal member 1. Those skilled in the art will appreciate that the edge defined by the tapering curve 6 may be, for example, a straight line, or a series of straight lines, and may intersect the tangent line 5 at angles other than perpendicular or near perpendicular.

The tangent line 5 defines a break in the major plane 2 of the distal member 1 wherefrom a flange 9 extending beyond the tangent line 5 toward the thumb-facing edge of the distal member 1 curves away from the major plane 2 and toward the first metacarpal 101 (thumb). The radial focal line of the curve of the flange 9 is preferably the long axis of the index metacarpal 100. A first mounting hole 10 defined through the thickness of the distal member 1 is preferably located in the flange 9 near the second end 8 of the distal member 1, the axis of which first mounting hole 10 is preferably a radius of the curvature of the flange 9. A second mounting hole 11 defined through the thickness of the distal member 1 is preferably located in the major plane 2 of the distal member 1 proximally to the first mounting hole 10 but closer to the first end 3 of the distal member 1, the axis of which second mounting hole 11 is preferably perpendicular to the major plane 2 of the distal member 1. A third mounting hole 12 defined through the thickness of the distal member 1 may be preferably located in the flange 9 proximally to the second mounting hole 11, but closer to the first end 3 of the distal member 1, the axis of which third mounting hole 12 is preferably a radius of the curvature of the flange 9. Preferably, none of the axes of the mounting holes 10 11 & 12 share, with respect to tangent line 5, a longitude or latitude, and the axis of each of the mounting holes 10 11 & 12 preferably focuses radially on the long axis of the index metacarpal 100. As seen in FIG. 12, the distal member 1 is preferably of sufficient length that the center point of the semicircle of the first end 3 is located generally over the virtual rotational center of the proximal carpal bones 103 of the wrist and the axes of the mounting holes 10 11 & 12 focus generally on the proximal two-thirds of the index metacarpal 100. Those skilled in the art will appreciate that the number, location, and orientation of the mounting holes may vary as required for optimal pin placement.

The first end 3 of the distal member 1 is preferably provided with a keyed post 13 that allows pivotable keyhole-type engagement with the first end 32 of the pivot member 30, described below. The keyed post 13 extends out of the major plane 2 along the central axis of the semicircle.

Alternatively, as in FIGS. 3A-3B, the first end 3 of the distal member 1 is provided with a plurality of arc-shaped flanges 15 to permit snap-in pivotable engagement with the first end 32 of the pivot member 30 to form the dorsal hinge. The flanges 15 extend out of the major plane 2 along the central axis of the semicircle. A protruding lip 14 extends across the width of each flange 15 and tapers to an edge defining the free end of each flange 15.

As may be seen in FIGS. 4A-4C, 12 and 13 the pivot member 30 functions primarily to orient the major plane 51 of the distraction member 50 and major plane 74 of the radial member 70 preferably generally perpendicularly to the major plane 2 of the distal member 1. The plane 31 of the first end 32 of the pivot member 30 is preferably coplanar with the major plane 2 of the distal member 1; that is, the plane 31 of the first end 32 is generally parallel to the dorsal aspect of the hand. The plane 33 of the second end 34 of the pivot member 30 is generally perpendicular to the plane 31 of the first end 32.

For the keyhole engagement system, a first keyed pivot hole 35 defined through the thickness of the pivot member 30 and further defined to accept the keyed post 13 of the distal member 1 (not shown), is located near the first end 32, the axis of which first keyed pivot hole 35 is generally perpendicular to the plane 31 of the first end 32. A second keyed pivot hole 36 defined through the thickness of the pivot member 30 and further defined to accept the keyed post 60 of the distraction member 50 (not shown), is located near the second end 34, the axis of which second keyed pivot hole 36 is generally perpendicular to the plane 33 of the second end 34. The axes of the first keyed pivot hole 35 and second keyed pivot hole 36 may lie in a common geometric plane.

As seen in FIGS. 5A-5B, for the snap-in engagement system, the first pivot hole 37 is formed to accept the flanges 15 of the distal member 1 (not shown), and the second pivot hole 38 is formed to accept the flanges 58 of the distraction member 50 (not shown).

The distraction member 50 provides a means for selective distraction of the arm, wrist and/or hand bones, as seen in FIGS. 6A-6D and 13. The major plane 51 of the distraction member 50 is oriented generally perpendicularly to the major plane 2 of the distal member 1. The distraction member 50 is generally planar, and is defined along its long axis by generally parallel edges 52 defining the width of the distraction member 50. The distraction member 50 is further defined at a first end 53 by a semicircle, the center point of which lies upon the long axis, and at the second end 54 by a straight edge 55 that preferably angularly intersects the parallel edges 52. Those of skill in the art will appreciate that the width of the distraction member 50 need not be defined by parallel edges 52, but may be defined, for example, by curved edges or non-parallel edges. Those skilled in the art will also appreciate that the straight edge 55 may be, for example, curved, or comprised of multiple straight edges or curves, and may intersect the parallel edges 52 at any angle.

The first end 53 of the distraction member 50 is preferably provided with a keyed post 60 that allows pivotable keyhole-type engagement with the second end 34 of the pivot member 30 (not shown). The keyed post 60 extends out of the major plane 51 along the central axis of the semicircle.

Again, as seen in FIGS. 7A-7B, for the snap-in engagement system, the first end 53 of the distraction member 50 is provided with a plurality of arc-shaped flanges 58 to permit snap-in pivotable engagement with the second end 34 of the pivot member 30 (not shown). The flanges 58 extend out of the major plane 51 along the centerline axis of the semicircle. A protruding lip 59 extends across the width of each flange 58 and tapers to an edge defining the free end of each flange 58.

The drawings and the present description address a keyhole engagement system and a snap-in engagement systems allowing for pivotable engagement. Those skilled in the art will recognize other means of pivotable engagement, such as by bolt or rivet, or other customary engagement means, may be utilized to pivotably engage the first end 3 of the distal member 1 to the first end 32 of the pivot member 30, and the first end 53 of the distraction member 50 to the second end 34 of the pivot member 30.

Within the distraction member 50, two spaced-apart rail holes 56 are defined to lie parallel to and along the long axis and extend into, but not through, the thickness of the distraction member 50 from the straight edge 55. Each rail hole 56 is preferably of a constant diameter, and preferably has a smooth bore.

Further within the distraction member 50 is defined a distraction hole 57 extending along the long axis completely through the distraction member 50. Distraction hole 57 may be threaded to accept a screw, such as screw 91 (not shown), or defined to receive a nut (not shown) through which a screw may be threaded.

The radial member 70, as seen in FIGS. 8A-8D, 12 and 13, is provided with multiple points for fixation of the fixator to the radius bone 104. The long axis of the radial member 70 is aligned with the long axis of the distraction member 50 (not shown) such that radial member 70 and major plane 51 of the distraction member 50 are generally coplanar. At a first end 71 of the radial member 70 is a straight edge 72 fashioned and oriented to complement the angled straight edge 55 of the distraction member 50. The second end 73 of the radial member 70 generally tapers toward a narrow radius. The surface of the radial member 70 curves gradually out of the major plane 74 to generally follow the curvature of the pivot member 70 and to generally conform to the lower arm. A first mounting hole 75 defined through the thickness of the radial member 70 is preferably located near the second end 73 of the radial member 70, the axis of which first mounting hole 75 is preferably a radius of the curvature of the radial member 70. A second mounting hole 76 defined through the thickness of the radial member 70 is preferably located in the major plane 74 proximally to the first mounting hole 75 but closer to the first end 71 of the radial member 70, the axis of which second mounting hole 76 is preferably perpendicular to the major plane 74 of the radial member 70. A third mounting hole 77 defined through the thickness of the radial member 70 is preferably located proximally to the second mounting hole 76, but closer to the first end 71 of the radial member 70, the axis of which third mounting hole 77 is preferably a radius of the curvature of the radial member 70. As seen in FIGS. 12 and 13, the axes of each of the mounting holes 75 76 & 77 generally focus radially on the long axis of the radius bone 104. The radial member 70 is preferably of such a length that, when assembled with the distraction member 50 (not shown), the pins 92 may be set within the distal half of the radius bone 104. Those skilled in the art will appreciate that the number, location, and orientation of the mounting holes may vary as required for optimal pin placement.

The radial member 70 further defines rail holes 78 to lie parallel to the long axis and extend into, but not through, the radial member 70, and correspond coaxially to the rail holes 56 of the distraction member 50 (not shown). Each rail hole 78 is preferably of a constant diameter, and preferably has a smooth bore.

As seen in FIGS. 1A-1F, the distal member 1, pivot member 30 and distraction member 50 are assembled to permit the wrist to move through a substantially normal range of motion. For keyhole pivotable engagement, the keyed post 13 of the distal member 1 is inserted through the first pivot hole 35 of the pivot member 30, and the distal member 1 is rotated sufficiently to capture the keyed post 13 within the first pivot hole 35. Likewise, for the distraction member 50, the keyed post 60 is inserted through the second pivot hole 36 of the pivot member 30, and the distraction member 50 is rotated sufficiently to capture the keyed post 60 within the second pivot hole 36.

For snap-in pivotable engagement, the flanges 15 of the first end 3 of the distal member 1 are urged into one side of the first pivot hole 37 of the pivot member 30 so that the lip of each flange 15 clears the far side of the first pivot hole 37 such that the distal member 1 may not be removed from the pivot member 30 unless the free ends of the flanges 15 are simultaneously urged toward the centerline axis of the first pivot hole 37. The flanges 58 of the first end 53 of the distraction member 50 are urged into one side of the second pivot hole 38 at the second end 34 of the pivot member 30 so that the lip of each flange 58 clears the far side of the second pivot hole 38 such that the distraction member 50 may not be removed from the pivot member 30 unless the free ends of the flanges 58 are simultaneously urged toward the centerline axis of the second pivot hole 38.

It will be appreciated by those skilled in the art that the pivot member may be provided with the key posts 13 & 60 and the distal and distraction members 1 & 50 may be provided with corresponding "keyholes," in other words reversing the relative position of the constituent keyhole engagement parts. Those skilled in the art will appreciate that the same may be accomplished for the flanges and holes of the snap-in engagement system.

Figure 1E:
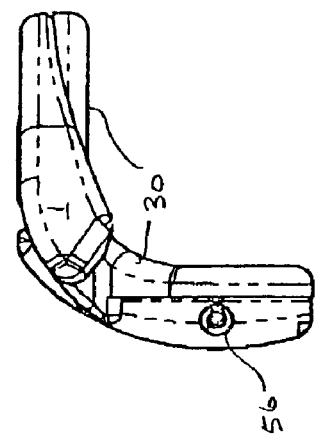
Figure 1C:
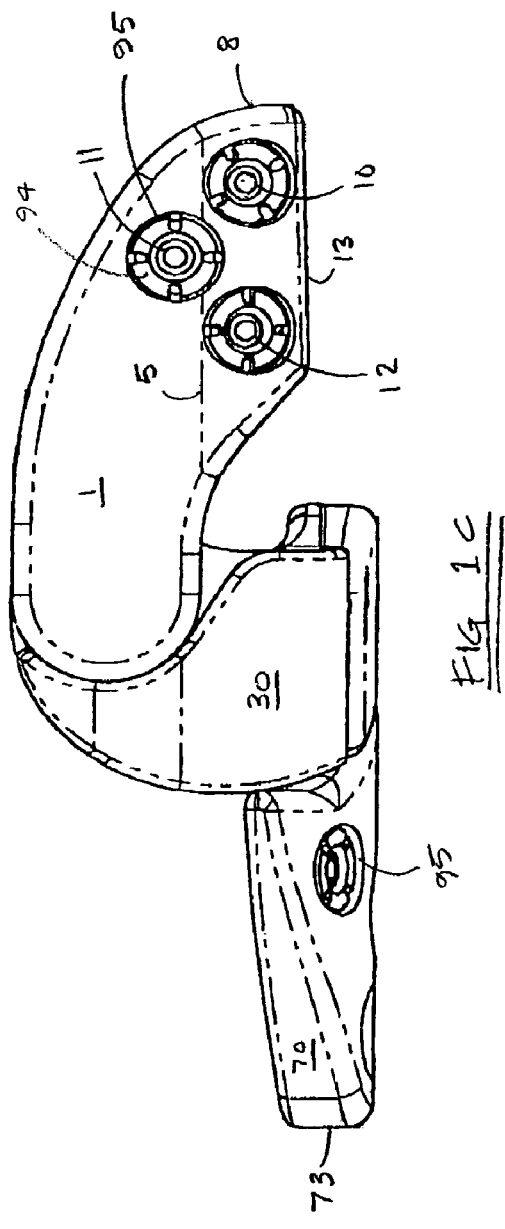
Figure 1D:
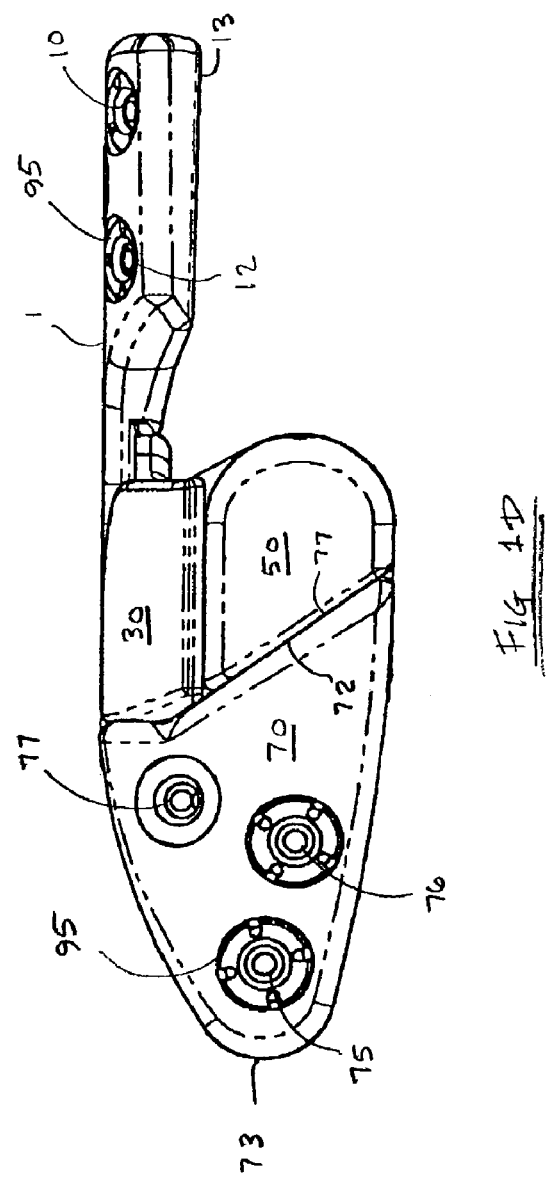
Figure 1F:
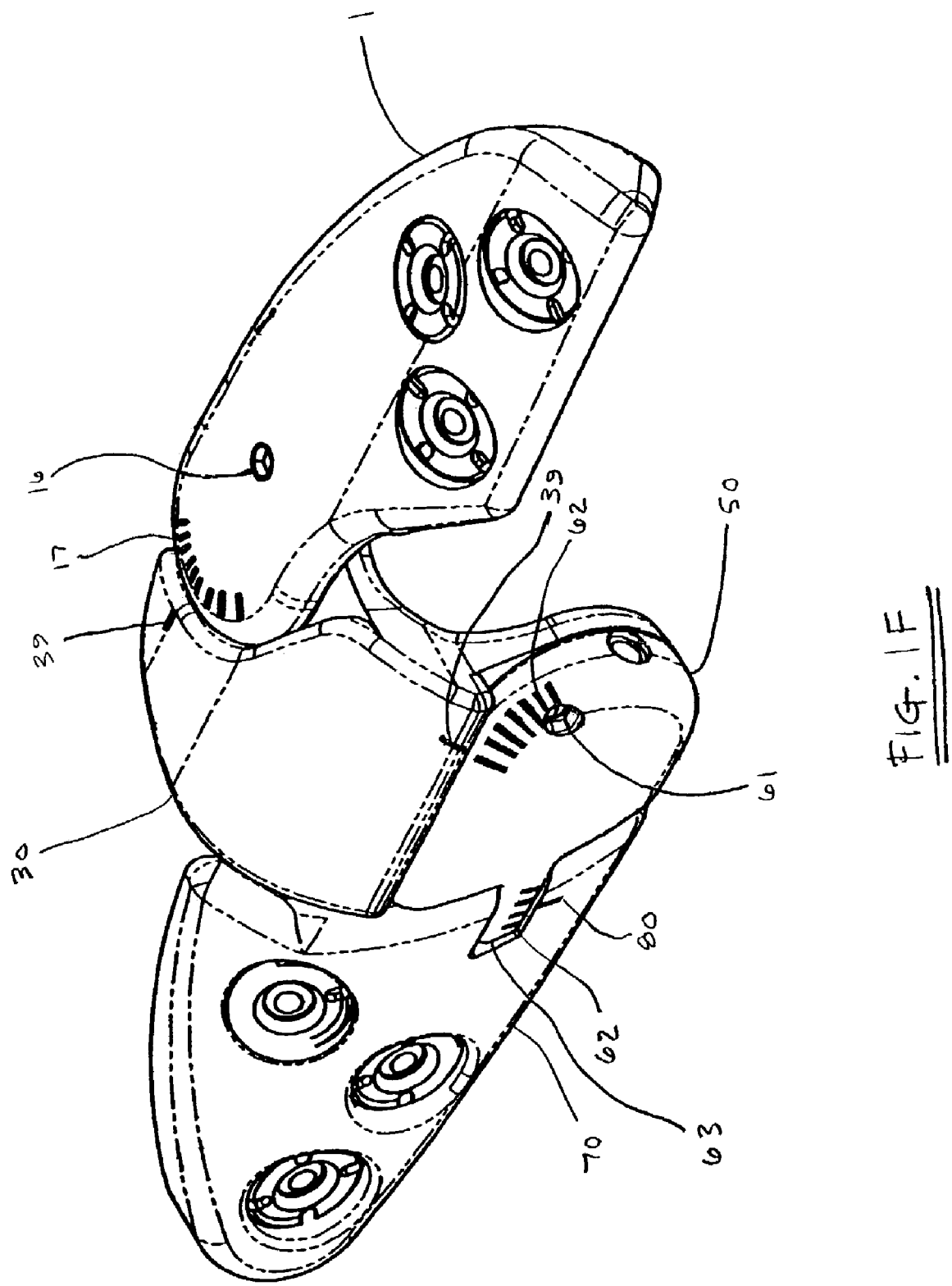
FIG. 1F depicts, for an assembled fixator of the present invention, the preferred orientation of graduations and preferred locations of set screws.
Figure 4B:
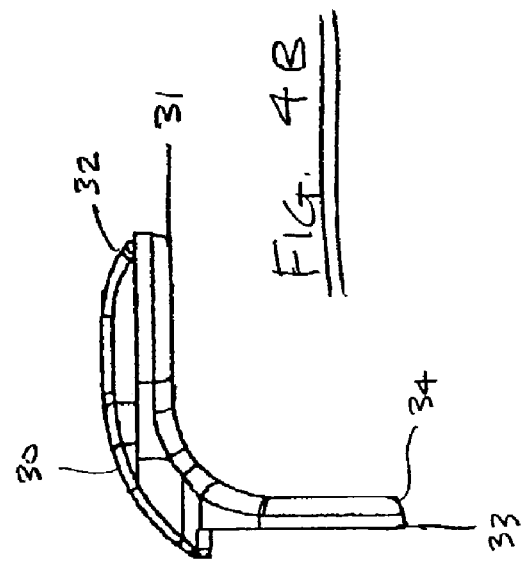
FIGS. 4A-4C are various views of the pivot member, in a keyhole engagement embodiment.
Figure 4C:
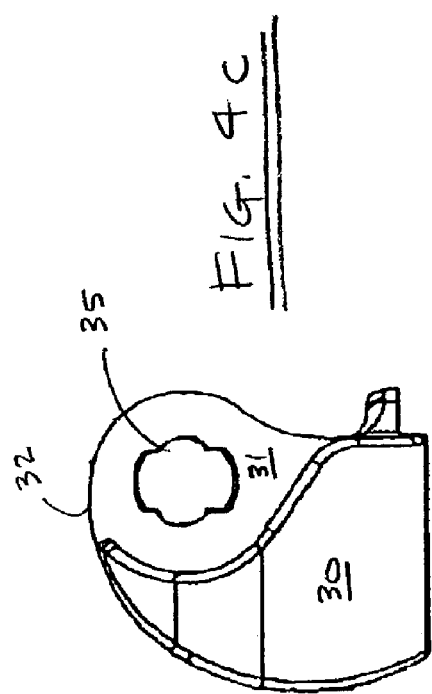
Figure 4A:
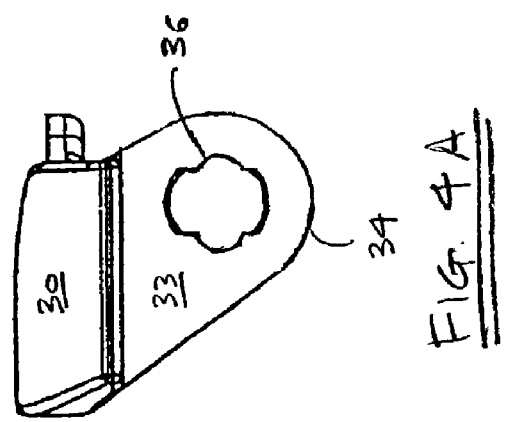

The angular relationship of the distal member 1 to the pivot member 30, and the angular relationship of the distraction member 50 to the pivot member 30, may be indicated by graduations 17, 39 & 62 formed into, or otherwise affixed to those members, as seen in FIG. 1F. Angular displacement of the distal member 1 relative to the pivot member 30, and the angular displacement of the distraction member 50 relative to the pivot member 30 may be limited or prevented by adjustment of set screws 16 & 61 provided in distal member 1 and distraction member 50, respectively. The set screws 16 & 61 are preferably threaded through the thickness of the distal and distraction members 1 & 50, respectively, to engage the pivot member 30. The pivot member 30 is preferably provided with multiple depressions or recesses (not shown) into which the set screws 16 & 61 may extend so as to fix the relationship of the members.

Two rails 90, as seen in FIG. 11, are provided for translational connection of the distraction member 50 to radial member 70. Each rail 90 is preferably press fit at one end into a rail hole 56 of the distraction member 50, and preferably slidably inserted at the other end into a corresponding rail hole 78 of the radial member 70 so as to permit translational movement. At a first extreme of translational movement, travel will cease when the respective straight edges 52 & 72 of the distraction member 50 and radial member 70 complementally abut. At the second extreme of translational movement, the distraction member 50 and radial member 70 are separated until the radial member 70 is completely disengaged from a rail 90. The rails 90 may be comprised of, for example, stainless steel or radiolucent material. The rails 90 are preferably of constant diameter. It is preferred that the rails 90 fit snugly into the rail holes 78 of the radial member 70 to minimize any looseness, or "play" of the rails 90 within the holes 78 to prevent undesired misalignment of the fracture. Those skilled in the art will appreciate that a single rail, having a circular or polygonal cross-section, may be utilized in place of multiple rails.

Between the first and second extremes of translational movement, the minimum distance separating the distraction member 50 and radial member 70 may be adjusted by advancing a screw 91 through the distraction hole 57 of the distraction member 50 toward the radial member 70 such that the screw 91 protrudes from the distraction member 50 to abut the radial member 70 at a divot 79 preferably provided in the radial member 70. The screw 91 may be comprised of, for example, stainless steel or radiolucent material. It will be appreciated that the screw 91 may perform the distraction member-to-radial member alignment function of a rail 90.

For visual indication of the relative position of, or distance of distraction between the distraction member 50 and the radial member 70, a graduated tab 63 may be formed into, or otherwise affixed to the distraction member 50 to extend to the radial member 70 such that the graduations 62 on the graduated tab 63 correspond to graduations 80 associated with the radial member 70, as seen in FIG. 1F. The graduated tab 63, of course, may be formed into, or otherwise affixed to the radial member 70 to correspond to graduations 62 associated with the distraction member 50.

In the present invention, the respective mounting holes 10, 11, 12, 75, 76 & 77 of the distal member 1 and radial member 70 are each preferably defined within wells 95 defined in those distal 1 and radial 70 members, into each of which well a ball cap 94, as seen in FIGS. 9A-9B, may be threadably inserted to immovably trap and fix a pin ball 93, seen in FIGS. 10A-10B, around the shank of a pin 92 such that the pin 92 is prevented from sliding through the pin ball 93, as seen in FIGS. 12 and 13. This manner of mounting the fixator to the hand and arm tolerates imprecise pin 92 placement in the bone, and allows the distance between the fixator and the arm, wrist and/or hand to be appropriately set by sliding the pin ball 93 up or down the pin 92 before the ball cap 94 is advanced into the well 95 to immovably trap the pin ball 93. Both ball cap 94 and pin ball 93 are preferably comprised of radiolucent polycarbonate material, but may be of any suitable non-radiolucent material.

The dynamic external fixator of the present invention is preferably comprised, either in whole or in part, of radiolucent material. Such radiolucent material is preferably polycarbonate material.

The present invention may be scaled up or down in size to accommodate variations in human anatomy. Accordingly, it is preferred that the fixator be manufactured in sizes to accommodate, for example, a large adult, a small adult and a child. Additionally, those skilled in the art will recognize that a dynamic external fixator for one hand may be constructed, mirrored geometrically, for affixation to the other hand.

USE OF THE DYNAMIC EXTERNAL FIXATOR

The dynamic external fixator of the present invention is attached to the lower arm and hand by an accepted and well-known method of using elongate pins adapted at one end for affixation in bone, such as described below.

A folded standard operating room sterile towel or lap sponge is used to establish a preferably one-fourth inch distance between the fixator and the skin of the patient. Care is taken to avoid contact between the skin of the patient and the fixator.

The fixator is positioned over the arm and hand such that the pivot hole 35 is coaxial with the virtual center of rotation for lateral flexion of the hand, and the pivot hole 36 is coaxial with the virtual center of rotation for palmar-dorsal flexion of the hand. This arrangement permits the wrist and fixator to move together. Wrist/fixator motion, i.e, the relative motion between the distraction member and pivot member, and distal member and pivot member, may be limited or prevented by adjustment of the hinge set screws.

The fixator is further positioned over the arm and hand such that the third hole of the distal member is preferably placed over the tendon of insertion of the extensor carpi radialis longus overlying the metaphyseal base of the index metacarpal. An insertion immediately proximal to the fibers of the first dorsal interosseous muscle avoids inadvertent insertion into the carpometacarpal joint.

A pin is inserted through the third mounting hole of the distal member and driven under radiographic assistance into the index metacarpal to a secure and proper depth. The distance between the fixator and the patient's skin can be adjusted and fixed by sliding the pin ball along the shaft of the pin and trapping it in the well of the third hole by threading the ball cap into the well. Pins may be placed through remaining available mounting holes in bone at appropriate places as needed, and the fixator affixed to them as described.

Distraction of the wrist bones is accomplished by threadably advancing the screw through the distraction hole of the distraction member to abut the radial member and force the distraction and radial members apart along the direction of the rails.

I claim:

1. An external fixation device for facilitating the healing and repair of bone fractures of the hand, wrist and lower arm, the device comprising:
    (a) a distal member comprising a dorsal pivotal engagement hub and defining a mounting aperture,
    (b) a pivot member comprising a first pivotal engagement hub and a second pivotal engagement hub, wherein the rotational axes of said first and second hubs are generally orthogonal,
    (c) a distraction member comprising a lateral pivotal engagement hub, and
    (d) a radial member defining a mounting aperture,
    wherein said dorsal pivotal engagement hub of said distal member is connected to said first pivotal engagement hub, forming a revolute joint, to define lateral flexion of the hand with respect to the lower arm, said lateral pivotal engagement hub of said distraction member is connected to said pivot member at said second pivotal engagement hub, forming a revolute joint to allow said distraction member to rotate with respect to said pivot member, to define palmer-dorsal flexion of the hand with respect to the lower arm, and said radial member translationally connected to said distraction member; and
    wherein said distal member and said radial member further define a well coaxial with said mounting aperture.

2. The device of claim 1, further comprising:
    (a) a guide rail, and
    (b) a distraction screw wherein said guide rail is disposed partially within said radial member and partially within said distraction member to allow translation of said radial member along said guide rail, and said distraction screw is disposed through said distraction member such that advancement of said distraction screw will urge said distraction member and said radial member apart.

3. The device of claim 1, wherein said dorsal engagement hub and said first pivotal engagement hub, and said lateral engagement hub and said second pivotal engagement hub, are adapted to form said revolute joints by snap-in engagement.

4. The device of claim 1, wherein said dorsal engagement hub and said first pivotal engagement hub, and said lateral engagement hub and said second pivotal engagement hub, are adapted to form said revolute joints by keyhole engagement.

5. The device of claim 1, said distal member and said distraction member each further comprising a set screw disposed so as to engage said pivot member.

6. The device of claim 5, said pivot member further comprising a plurality of recesses into which said set screws may extend.

7. The device of claim 1, said distal member further comprising graduations and said pivot member further comprising graduations, said graduations of said distal member oriented to correspond to said graduations of said pivot member to provide a visual indication of the relative angular relationship of said distal member and said pivot member.

8. The device of claim 1, said distraction member further comprising graduations and said pivot member further comprising graduations, said graduations of said distraction member oriented to correspond to said graduations of said pivot member to provide a visual indication of the relative angular relationship of said distraction member and said pivot member.

9. The device of claim 1, said distraction member further comprising a graduated tab extending therefrom adjacent said radial member, said radial member further comprising graduations oriented to correspond to said graduated tab to provide a visual indication of the relative distance between said radial member and said distraction member.

10. The device of claim 1, wherein said distal member, said pivot member, said distraction member, and said radial member are radiolucent.

11. The device of claim 1, wherein said distal member, said pivot member, said distraction member, and said radial member are transparent.

12. The device of claim 1, wherein said distal member, said pivot member, said distraction member, and said radial member substantially conform to the human lower arm and hand in a low-profile and aesthetic manner.

13. The device of claim 1, further comprising a pin ball and ball cap, wherein an elongate pin may be slidably disposed through said pin ball and one of said mounting apertures, and said pin ball may be trapped within said well by said ball cap such that both pin ball and said elongate pin are rendered immovable by unaided human force and wherein said elongate pin may be positioned so as to be affixed at one end to a human bone.

14. A method for facilitating the healing and repair of a distal radius bone fracture, the method comprising the steps of:
  (a) affixing a plurality of spaced-apart elongate pins in the radius on the proximal side of the fracture,
  (b) affixing a plurality of spaced-apart elongate pins in a metacarpal on the distal side of the fracture, and
  (c) mounting an external wrist fixator to said pins, wherein said mounting step comprises for each of said plurality of pins the following steps, in order:
    1. guiding said pin through a mounting aperture defined in said fixator,
    2. guiding a pin ball onto said pin through a central bore of said pin ball,
    3. sliding said pin ball along said pin to seat said pin ball within a well associated with said mounting aperture, and
    4. fixing said pin ball within said well by use of a ball cap such that said pin and said pin ball are rendered immovable.

15. A method for facilitating the healing and repair of a distal radius bone fracture, the method comprising the steps of:
  (a) affixing a plurality of spaced-apart elongate pins in the radius on the proximal side of the fracture,
  (b) affixing a plurality of spaced-apart elongate pins in a metacarpal on the distal side of the fracture,
  (c) mounting an external wrist fixator to said pins, said fixator comprising:
    1. a distal member,
    2. a pivot member comprising a first pivotal engagement hub and a second pivotal engagement hub,
    3. a distraction member,
    4. a radial member,
    wherein said distal member is pivotally connected to said pivot member at said first pivotal engagement hub, said distraction member is pivotally connected to said pivot member at said second pivotal engagement hub to allow rotation of said distraction member with respect to said pivot member, and said radial member is translationally connected to said distraction member; and
  (d) guiding a said pin through a mounting aperture defined in said fixator,
  (e) guiding a pin ball onto said pin through a central bore of said pin ball,
  (f) sliding said pin ball along said pin to seat said pin ball within a well associated with said mounting aperture, and
  (g) trapping said pin ball within said well by use of a ball cap such that said pin and said pin ball are rendered immovable by unaided human force.

16. The method of claim 15, wherein said external fixator further comprises
  (a) a guide rail, and
  (b) a distraction screw, wherein said guide rail is disposed partially within said distraction member and partially within said radial member, and said distraction screw is disposed through said distraction member, and said method further comprises the step of advancing said distraction screw to urge said distraction member and said radial member apart.

17. The method of claim 15, wherein said external fixator comprises
  (a) a distal member comprising a dorsal engagement hub and defining a mounting aperture,
  (b) a pivot member comprising a first pivotal engagement hub and a second pivotal engagement hub, wherein the rotational axes of said first and second hubs are generally perpendicular,
  (c) a distraction member comprising a lateral engagement hub,
  (d) a radial member defining a mounting aperture, wherein said dorsal engagement hub of said distal member is connected to said pivot member at said first pivotal engagement hub, forming a revolute joint to define lateral flexion of the hand with respect to the lower arm, said lateral engagement hub of said distraction member is connected to said pivot member at said second pivotal engagement hub, forming a revolute joint, to define palmar-dorsal flexion of the hand with respect to the lower arm, and said radial member is translationally connected to said distraction member.

18. The method of claim 17, wherein said fixator further comprises (a) a guide rail, and
(b) a distraction screw wherein said guide rail is disposed partially within said radial member and partially within said distraction member to allow translation of said radial member and said distraction member along said guide rail, and said distraction screw is disposed through said distraction member, and said method further comprises the step of advancing said distraction screw to urge said distraction member and said radial member apart.

* * * * *